(12) United States Patent
Sunagawa et al.

(10) Patent No.: US 9,242,096 B2
(45) Date of Patent: Jan. 26, 2016

(54) STIMULATION DEVICE AND METHOD FOR TREATING CARDIOVASCULAR DISEASE

(71) Applicant: KYUSHU UNIVERSITY, NATIONAL UNIVERSITY CORPORATION, Fukuoka (JP)

(72) Inventors: Kenji Sunagawa, Fukuoka (JP); Tomomi Ide, Fukuoka (JP)

(73) Assignee: KYUSHU UNIVERSITY, NATIONAL UNIVERSITY CORPORATION, Fukuoka (JP)

( * ) Notice: Subject to any disclaimer, the term of this patent is extended or adjusted under 35 U.S.C. 154(b) by 0 days.

(21) Appl. No.: 14/197,441

(22) Filed: Mar. 5, 2014

(65) Prior Publication Data
US 2015/0025591 A1   Jan. 22, 2015

Related U.S. Application Data

(63) Continuation-in-part of application No. 13/257,583, filed as application No. PCT/JP2010/002016 on Mar. 19, 2010, now abandoned.

(60) Provisional application No. 61/161,456, filed on Mar. 19, 2010.

(51) Int. Cl.
*A61N 1/00* (2006.01)
*A61N 1/36* (2006.01)
*A61N 2/00* (2006.01)
*A61N 2/02* (2006.01)

(52) U.S. Cl.
CPC ........ *A61N 1/36114* (2013.01); *A61N 1/36053* (2013.01); *A61N 1/36167* (2013.01); *A61N 1/36153* (2013.01); *A61N 1/36171* (2013.01); *A61N 1/36175* (2013.01); *A61N 2/006* (2013.01); *A61N 2/02* (2013.01)

(58) Field of Classification Search
USPC ...................................... 607/9, 119
See application file for complete search history.

(56) References Cited

U.S. PATENT DOCUMENTS

2006/0100668 A1\* 5/2006 Ben-David et al. ............... 607/2
2008/0091255 A1   4/2008 Caparso et al.
2008/0300642 A1  12/2008 Inagaki et al.

FOREIGN PATENT DOCUMENTS

JP   2005-500863 A    1/2005
JP   2008-296014 A   12/2008
JP   2009-233024 A   10/2009
(Continued)

OTHER PUBLICATIONS

Magstim Air-Cooled Double 70mm Coil System: Operating Manual 1600-23-04, The Magstim Company Limited U.K., 1999.
(Continued)

*Primary Examiner* — Nicole F Lavert
(74) *Attorney, Agent, or Firm* — Konomi Takeshita

(57) ABSTRACT

An electrical stimulation device and method are provided for treating cardiovascular disease in a human or an animal, the device including at least one electrode configured for placement on a nerve site inside the human or the animal, the at least one electrode having a spherical shape, and an electrical stimulation application unit coupled to the at least one electrode and configured to apply electrical stimulation to a vagus nerve in a neck region of the human or the animal by the at least one electrode.

11 Claims, 10 Drawing Sheets

(56) References Cited

FOREIGN PATENT DOCUMENTS

| | | |
|---|---|---|
| WO | 02/45791 A2 | 6/2002 |
| WO | 2008/045434 A2 | 4/2008 |

OTHER PUBLICATIONS

Chris Hovey BSc and Reza Jalinous PhD, The Guide to Magnetic Stimulation, The Magstim Company Limited U.K. Jul. 21, 2006.

Reza Jalinous, A Guide to Magnetic Stimulation, The Magstim Company Limited, U.K. Mar. 1, 1998.

Vol. 4 Magnetic Stimulation Technical Note for Research, http://www.miyuki-net.co.jp/jp/seminar/msTechnicalNote/msTechnicalNote.shtml, MG Miyuki Giken, May 2012.

Takaki Tsutsumi et al, Modulation of the myocardial redox state by vagal nerve stimulation after experimental myocardial infraction. Cardiovascular Research Mar. 2008,1;77, 713-721.

Takaki Tsutsumi et al, Effect of anaesthesia-induced alterations in haemodynamics on in vivo kinetics of nitroxyl probes in electron spin resonance spectroscopy. Free Radical Research, Apr. 2008; 42(4): 305-311.

\* cited by examiner

STIMULATION DEVICE AND METHOD FOR TREATING CARDIOVASCULAR DISEASE

CROSS REFERENCE TO RELATED APPLICATIONS

This application is a continuation-in-part of U.S. patent application Ser. No. 13/257,583, filed on Feb. 3, 2012, which is a national phase application of PCT application No. PCT/JP2010/002016, filed on Mar. 19, 2010, which claims priority from U.S. provisional application Ser. No. 61/161,456, filed on Mar. 19, 2009.

FIELD OF THE INVENTION

The present invention relates to electrical and magnetic stimulation devices and methods for treating humans and animals with cardiovascular disease.

More specifically, the stimulation device for treating cardiovascular disease of the present invention applies stimulation to the vagus nerve in the neck region of a human or an animal. The stimulation can be generated electrically or magnetically.

BACKGROUND OF THE INVENTION

Myocardial infarction is a kind of ischemic heart disease, and is a state in which the amount of blood flow in coronary artery as nutrition to the heart drops, the heart muscle becomes ischemic and the heart dies. Normally, this refers to an acutely occurring "acute myocardial infarction (AMI)". The method of treatment during the acute phase is as a rule complete rest. During the acute phase after the onset of disease, it is easy for lethal arrhythmia to occur, and the danger of dying is extremely high. The more the ischemic period is prolonged, the more death of the heart muscle advances, and an irreversible decrease of cardiac performance occurs. When disease is first suspected, it is necessary to immediately call an ambulance while keeping an eye on the patient, and in the case that the patient become unconscious and there is no pulse, it becomes necessary to perform heart massage without hesitation. When functional cardiac arrest occurs, going three to five minutes or more without performing treatment results in a rehabilitation rate of nearly zero. It is necessary to start emergency treatment (heart massage or the like) without waiting for the ambulance to arrive.

Myocardial infarction is caused by insufficient relative and absolute oxygen supply to the heart muscle; and as a method of treatment, the patient is kept quiet in bed and oxygen inhalation is performed. In some cases morphine may also be administered in order to relieve pain and reduce oxygen consumption. The main objective during the acute phase is to prevent lesion expansion of myocardial infarction. Generally, the treatment performed as first aid for myocardial infarction is centered on "oral administration of aspirin", "oxygen inhalation", "administration of morphine" and "administration of nitrate", and is known by the name "MONA", taking the first letter from Morphine, Oxygen, Nitrate and Aspirin.

By actively performing reperfusion therapy of the obstructed coronary artery within six hours or less from the onset of the myocardial infarction, it is possible to reduce the range of necrosis of the heart muscle. Not being limited to this, in an example of a case within 24 hours from the onset of the illness, performing reperfusion therapy is highly meaningful. Generally, treatment may be divided into the case of performing catheter therapy (PTCA, PCI), or thrombolytic therapy (PTCR), and different treatment policies are adapted depending on the country, insurance or doctor's judgment. In Japan, many facilities are capable of performing PCI, and in many cases, PCI is performed during the acute phase. However, because examination and treatment are performed via an artery, complications often occur. Particularly, when a rise in ST is seen on the electrocardiogram, it is essential that PCI be performed as soon as possible, however, there are a few hospitals, even in the USA, which is a leading nation in the treatment of heart disease, that take the position of performing the same treatment immediately after the patient has been admitted to emergency. In the case of there being three or more sites of stenosis, there are some facilities that will perform emergency coronary artery bypass graft surgery (CABG). In comparing PCI and CABG, for PCI restenosis occurs in 25 to 30% of cases, so even in the case of single-vessel disease, there are cases where CABG has advantages. However, since 2004, drug-eluting stents (DES) are covered by insurance, so an improvement in the result of PCI treatment is expected. When intervention is successful during the acute phase, relative prognosis is often maintained. Intervention is one method for treating illness of the heart, blood vessels, the liver, the brain, digestive organs, urinary organs and the like, and is mainly a treatment method for performing treatment by inserting a small tube called a catheter into a blood vessel from a small hole having a diameter of several mm that is made in the skin. Intervention is a method of treatment that has very little burden on the patient, and recently has attracted much attention. The cut is small, so recovery after surgery is fast, and after a very short hospital stay of three to five days, together with greatly improving the QOL (Quality of Life) of the patient, this treatment reduces the financial burden on the patient, and is said to even contribute to health care cost-containment measures by the government. However, in reperfusion therapy such as intervention, complications such as arrhythmia, extrasystole, ventricular fibrillation, atrioventricular block or heart failure often occur.

Quick cardiovascular recovery is essential for maintaining life, however, exposes oneself to danger. Reperfusion increases localized damage, and produces an inflammatory reaction that also leads to systemic insult. Acute onset of myocardial infarction, stroke, cardiac arrest and the like can produce ischemia-reperfusion injury (IRI). However, many scheduled surgical treatments such as organ transplants and aneurysm treatment require a period of ischemia between treatments, and therefore may produce the onset of IRI. Conventionally it was thought that the existence of inflammatory cells in the ischemic tissue indicated a pathophysiological response to injury. However, according to laboratory tests, it has been shown that inflow to inflammatory cells, and particularly to macrophage tissue, which is a phagocyte, even though important for recovery, also brings about tissue damage that exceeds the tissue damage caused by ischemia alone. This damage can have an effect on various kinds of tissue such as the heart, brain, liver, spleen, intestines, lungs and pancreas.

Various methods for putting an end to reperfusion injury such as induced hypothermia, controlled reperfusion, ischemic preconditioning and the like have been reported. Induced hypothermia is the introduction of moderately low temperature (28° C. to 32° C.) to a patient. Mild induced hypothermia is thought to suppress many chemical reactions related to reperfusion injury. Regardless of these potential benefits, induced hypothermia also brings about side effects such as arrhythmia, infection, blood clotting and the like. Controlled reperfusion means to control the initial stage of reperfusion by performing reperfusion of tissue at low pressure using blood that has been altered so that there is hyperosmosis, alkalosis, and substrate concentration. Ischemic preconditioning is intentionally causing short-term ischemia, which has a protective effect, to occur by slowing down cellular metabolism between the onset of more prolonged ischemia. These treatments are useful in a surgical setting (for example, before or after scheduled heart surgery), however, normally, these treatments are not suitable in a preset condition that is controlled as required.

In recent years, applying electrical stimulation to the vagus nerve has been reported as an effective treatment method for chronic heart failure. In other words, when electrical stimulation of the vagus nerve is performed, the heart rate drops, and as the heart rate drops, the myocardial oxygen consumption is reduced, and a state of oxygen deprivation in the heart muscle is prevented or improved. As a result, the occurrence of myocardial ischemia and the accompanying lethal arrhythmia are prevented, so this method is considered to be effective as treatment for or prevention of heart failure. Technology has been disclosed related to a vagus nerve stimulation system for performing electrical stimulation of the vagus nerve, and particularly, technology has been disclosed related to a vagus nerve stimulation system that is capable of indirectly stimulating the vagus nerve from under the skin or from the surface of the skin (Japanese Patent Application laid-open publication No. 2005-500863, Japanese Patent Application laid-open publication No. 2009-233024).

DETAILED DESCRIPTION

Figure 1:
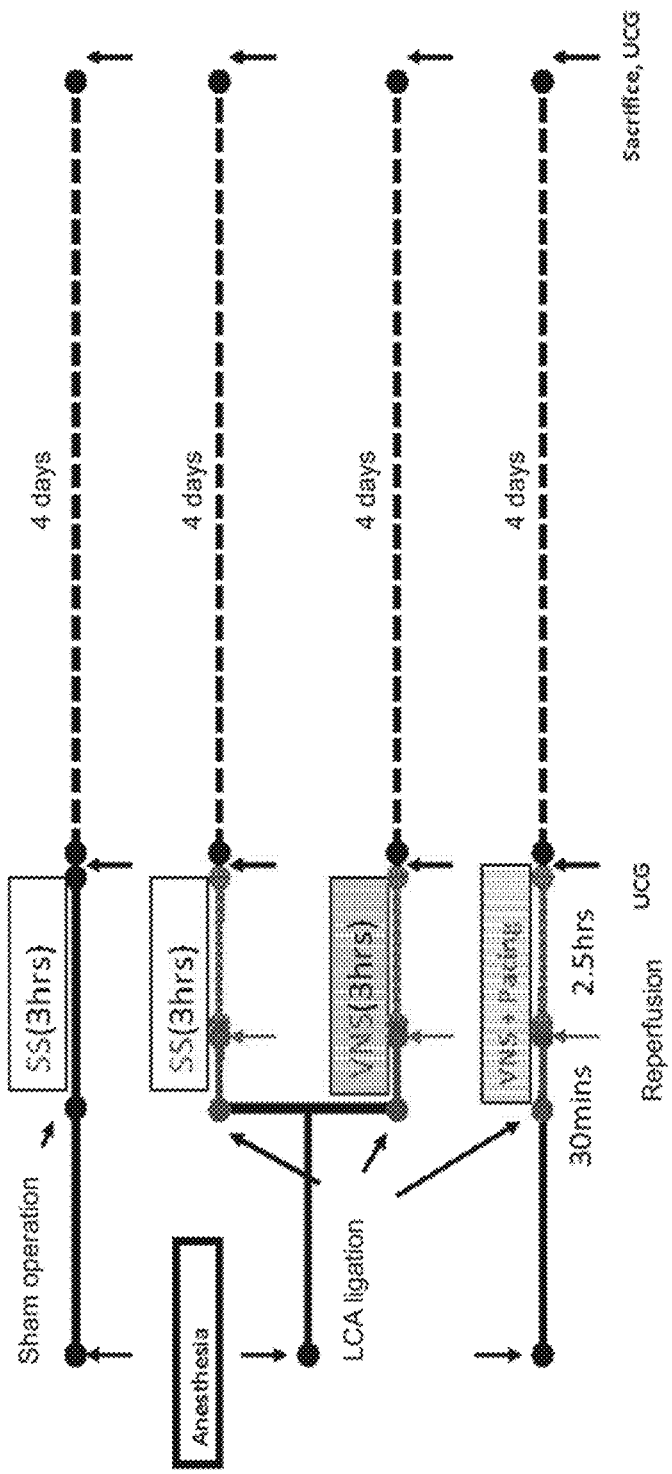
FIG. 1 illustrates the test protocol of an embodiment of the present invention.

Considering the above situation, the purpose of the present invention is to provide a new treatment method and device that are capable of improving a drop in myocardial contractility, suppressing the occurrence of arrhythmia, and reducing the size of infarction when treating cardiovascular disease such as acute myocardial infarction. The inventors took notice of the effect of treating cardiovascular disease by applying stimulation to vagus nerves.

Specifically, the present invention provides a treatment method and device for treating cardiovascular disease by applying electrical stimulation to the vagus nerve in the neck region of a human or an animal under specified conditions. By applying electrical stimulation to the neck region under certain conditions in this way, a superior treatment effect that prevents the occurrence of the above mentioned complications during treatment of cardiovascular disease becomes possible. By using the present invention to perform treatment by vagus nerve stimulation during emergency transport, it is possible to significantly lower the occurrence of complications after ischaemia reperfusion.

According to a first major aspect of the present invention, an electrical stimulation device for treating cardiovascular disease is provided that comprises at least one electrode that is placed on a nerve site inside a human or an animal, and an electrical stimulation application unit that applies electrical stimulation to the vagus nerve in the neck region of the animal by the electrode.

According to an embodiment of the present invention the electrical stimulation device for treating cardiovascular disease can be applied to treatment of acute myocardial infarction. The electrical stimulation device for treating cardiovascular disease of the present invention displays an excellent effect in the treatment of cardiovascular disease, particularly in the treatment of acute myocardial infarction.

Moreover, according to another embodiment of the present invention, the conditions for applying electrical stimulation when treating cardiovascular disease with the electrical stimulation can be a voltage of 0.1 to 5 V, a frequency of 1 to 30 Hz and a pulse width of 500 μsec. By applying electrical stimulation to the vagus nerve in the neck region under these conditions, it is possible to prevent complications that accompany treatment, and to obtain excellent therapeutic effect.

Furthermore, with another embodiment of the invention, the amount of time that electrical stimulation is applied using the electrical stimulation application unit can be at least 0.5 hour and no greater than 10 hours. By applying electrical stimulation for an amount of time within this range, effective treatment of cardiovascular disease is possible.

According to a second major aspect of the present invention, a method for treating cardiovascular disease in an animal is provided that comprises steps of: placing an electrode in contact with the vagus nerve in the neck region of a human or an animal; and applying an electrical stimulation by the electrode.

According to another embodiment of the present invention, the method for treating cardiovascular disease of this invention can be applied when the cardiovascular disease is acute myocardial infarction. The method for treating cardiovascular disease of the present invention particularly displays an effect when the cardiovascular disease is acute myocardial infarction.

Moreover, according to another embodiment of the present invention, it is possible for the step of applying an electrical stimulation of this method for treating cardiovascular disease to be used in combination with reperfusion therapy. By using the treatment method of this invention in combination with reperfusion therapy, even more effective treatment of cardiovascular disease can be expected. The step of applying an electrical stimulation of the present invention can be performed after the occurrence of acute myocardial infarction and before performing reperfusion therapy.

Furthermore, according to another embodiment of the present invention the conditions of a voltage of 0.1 to 5 V, a frequency of 1 to 30 Hz, and a pulse width of 500 μsec or greater can be applied as the conditions for applying electrical stimulation in the method for treating cardiovascular disease of this invention. By applying electrical stimulation under these conditions, it is particularly possible to perform effective treatment with no adverse effects such as complications.

In the following, the present invention will be described in detail. Any kind of device can be used as the electrical stimulation device for treating cardiovascular disease of the present invention as long as it is a device having at least one electrode that can be placed at the site of a nerve, and has an electrical stimulation unit for applying electrical stimulation to the vagus nerve of an animal by way of the electrode. The electrical stimulation unit can comprise, for example, a DC voltage generating circuit that generates a specified voltage, a capacitor that is charged by voltage that is generated by the DC voltage generating circuit, and a switch that is located between the capacitor and the electrode and that is for switching ON/OFF a connection between the capacitor and electrode.

In the electrical stimulation device for treating cardiovascular disease of the present invention, the electrode applies electrical stimulation by coming in direct contact with the vagus nerve of a human or an animal. Here, the vagus nerve refers mainly to a parasympathetic nerve that controls the internal organs of the thoracicoabdominal region, and also involved in adjustment of the heart rate, peristaltic movement of the stomach and intestines, perspiration, and speech. This vagus nerve runs from the brain stem to the abdominal region.

Figure 7:
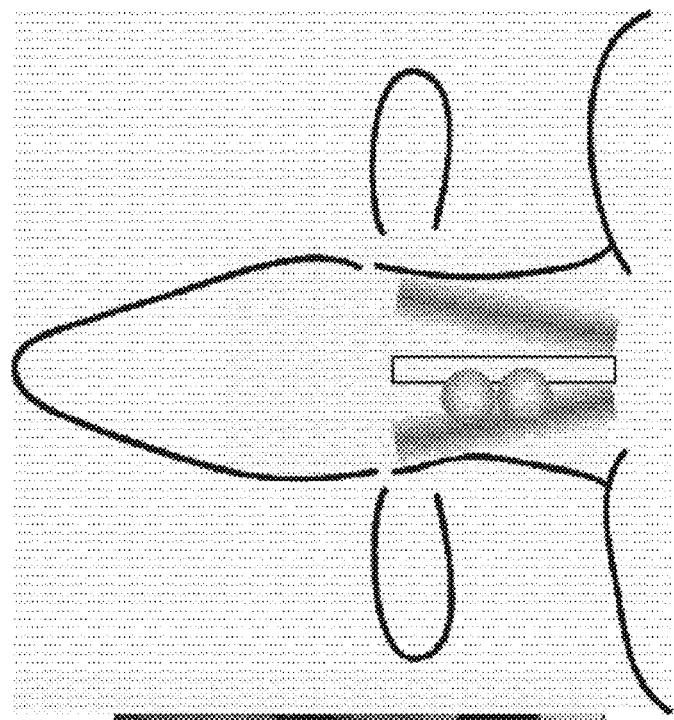
FIG. 7 is a drawing illustrating the site of electrical stimulation in an embodiment of the present invention.
Figure 7:
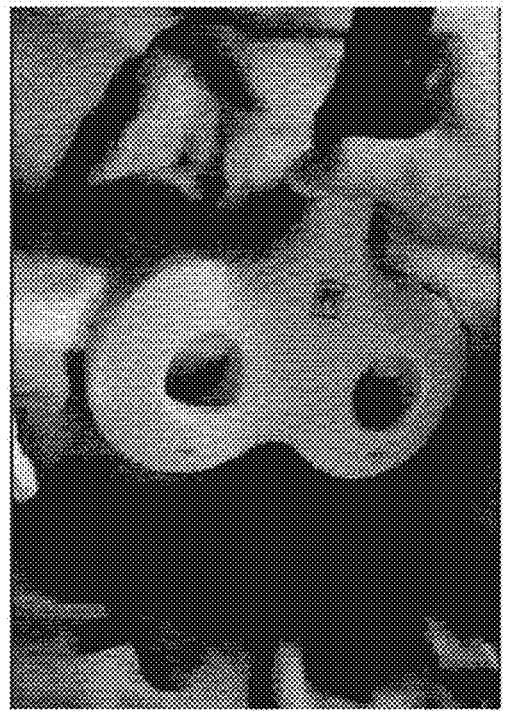
Figure 8:
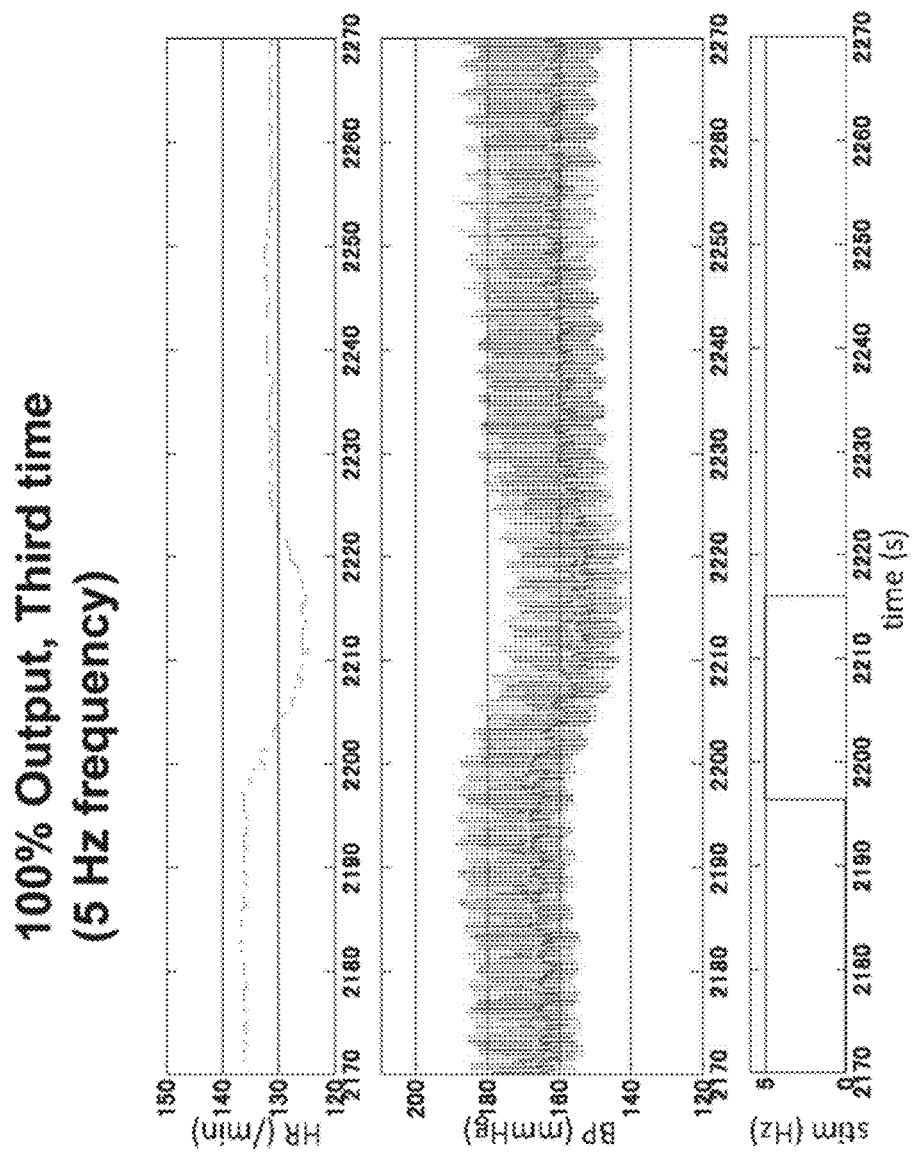
FIG. 8 is a drawing suggesting that, because the heart rate dropped when an existing magnetic stimulation device was applied to the neck region of a dog, the vagus nerve was stimulated by an electric field that was generated by generating a magnetic field.

In the present invention, the site of stimulation by the electrode is not particularly limited as long as it on a site of the vagus nerve, however, preferably the electrical stimulation is applied to the vagus nerve in the neck region. FIG. 7 illustrates the electrical stimulation site in the neck region in an embodiment of the present invention. When electrical stimulation is applied to a site of the vagus nerve by the electrode, the site of the vagus nerve to which the electrical stimulation is applied can be peeled back and exposed, for example, and the electrical stimulation can be applied by bringing the electrode in direct contact with the site. It is also possible to apply acupuncture stimulation to an acupuncture point that stimulates the vagus nerve, or apply electrical stimulation from inside a blood vessel.

The electrical stimulation device for treating cardiovascular disease of the present invention can be constructed with only an electrode and electrical stimulation application unit as described above, so from the aspect of compactness and convenience of operation, treatment by stimulation of the vagus nerve can even be performed during emergency transport. By being able to perform treatment by stimulation of the vagus nerve during emergency transport, it becomes possible to effectively lower the occurrence of complications after ischemia reperfusion.

The electrical stimulation device for treating cardiovascular disease of the present invention can be applied to various kinds of cardiovascular disease that are particularly treatable by stimulating the vagus nerve. For example, the device can be applied to treatment such as acute myocardial infarction, angina including unstable angina, heart failure, arrhythmia, hypertension, arteriosclerosis, and the like, and is particularly effective in the treatment of acute myocardial infarction and heart failure.

Conditions for applying electrical stimulation using the electrical stimulation device for treating cardiovascular disease of the present invention can be suitably set according to conditions that meet the severity of the patient's condition, and can be set within the range: a voltage of 0.01 to 20 V, frequency of 0.1 to 40 Hz, and pulse width of 500 μsec or greater. For example, in an embodiment of the present invention, conditions of a voltage of 0.1 to 5 V, frequency of 1 to 30 Hz, and pulse width of 500 μsec or greater are applied.

The time that electrical stimulus is applied in the present invention can be appropriately selected to correspond to the severity of the patient, however should be selected between 0.1 to 10 hours, or more preferably between 0.5 to 10 hours. The electrical stimulus can be applied intermittently at fixed time intervals, or can be applied continuously for a fixed time. After electrical stimulation has been applied for a fixed time, electrical stimulation can be applied again in the case that disease such as arrhythmia occurs.

Moreover, the method for treating cardiovascular disease of the present invention can be performed in combination with reperfusion therapy. When performed in combination with reperfusion therapy, the application of electrical stimulation can be performed before reperfusion therapy, can be performed at the same time as reperfusion therapy or can be performed after reperfusion therapy, however, preferably the electrical stimulation of the present invention is performed before performing the reperfusion therapy.

Figure 9:
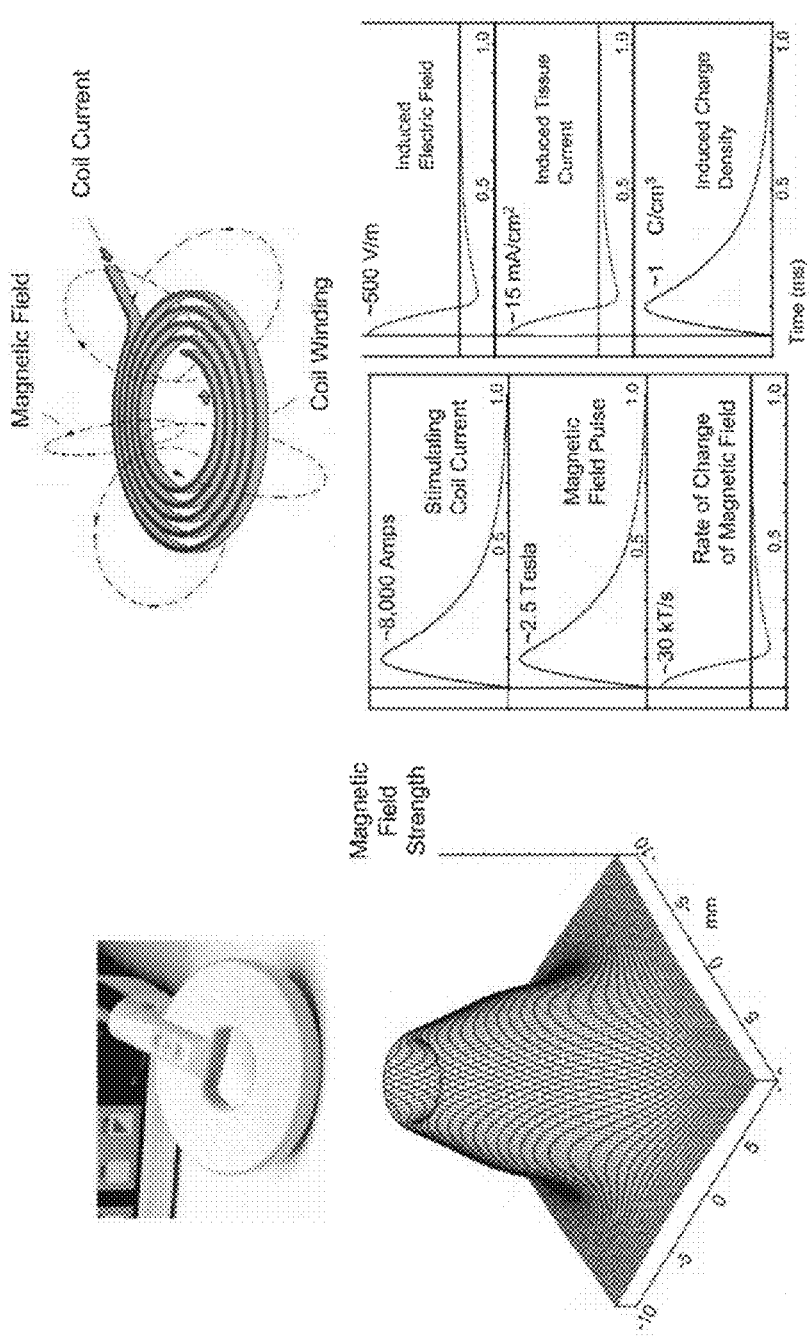
FIG. 9 is a drawing illustrating an example of a magnetic stimulation device that can be applied to the present invention.

Application of electrical stimulation is performed as the method for treating cardiovascular disease in the present invention, however, in addition to this, magnetic stimulation can also be used. For example, transcranial magnetic stimulation is performed using a magnetic stimulator that uses a coil for treating depression, however, by using a magnetic stimulation device to apply magnetic stimulation to the neck area of an animal, the same effects of lowering the heart rate and stimulating the vagus nerve can be obtained (FIG. 9).

Next, the effect of the present invention will be explained by illustrating an embodiment. However, the present invention is not limited to the embodiment described below, and it is understood that various changes and modification can be easily performed by one skilled in the art.

Embodiment 1

Thoracotomy was performed under anesthesia for a male SD rat, the left coronary artery was ligated, and after 30 minutes of ischemia, reperfusion was performed by loosening the ligature, which created myocardial infarction (MI). The right neck region was peeled to expose the vagus nerve, and stimulation of the vagus nerve was performed under the conditions of a 0 to 3V voltage, 1 msec pulse width and 5 Hz frequency so that a heart rate that was lowered by about 10% was obtained. Vagus nerve stimulation (VS), including reperfusion, was performed for 30 minutes from the time of ischemia, and after 24 hours, evaluations of the infarct area and apoptosis were performed, and after 4 days, evaluation of the hemodynamics was performed.

Figure 2:
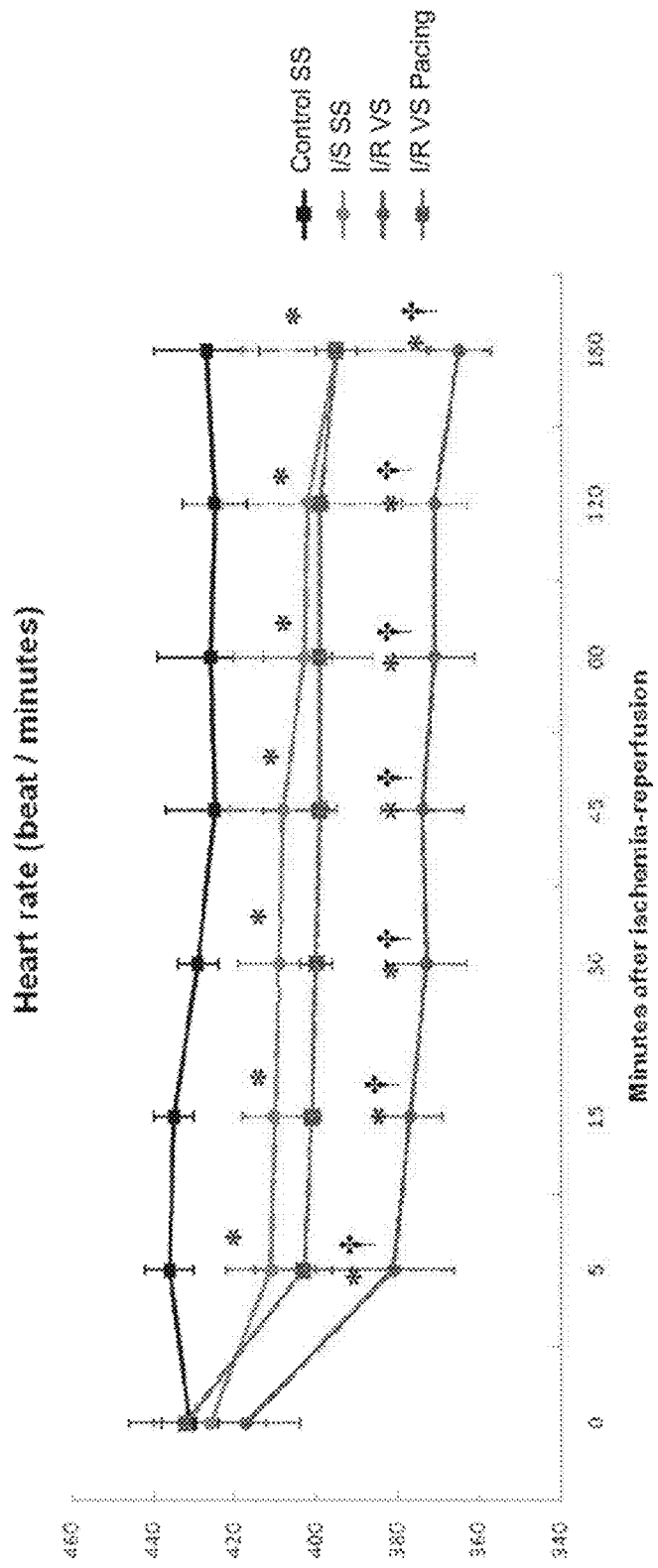
FIG. 2 is a graph illustrating the change in heart rate during stimulation of the vagus nerve in an embodiment of the present invention.

As a control, a group was made in which only a thoracotomy was performed, and as sham stimulation (SS), only an electrode was mounted without applying current. Moreover, in order to study the effect of bradycardia that occurs as the heart rate drops due to stimulation of the vagus nerve, pacing (VNS+pacing) was performed electrically in the right atrium during stimulation of the vagus nerve so that the heart rate could be maintained the same as in the SS group. The experimental protocol described above is illustrated in FIG. 1, and the change in the heart rate during stimulation of the vagus nerve is illustrated in FIG. 2.

Figure 3:
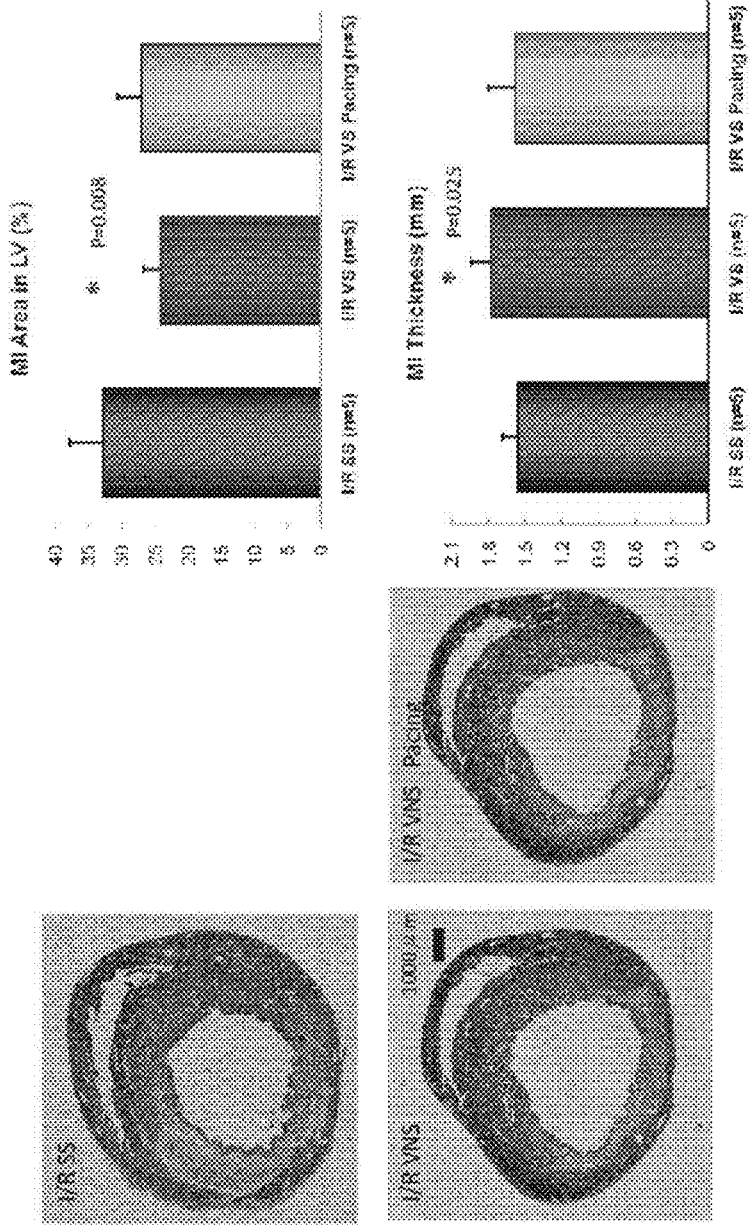
FIG. 3 is a drawing illustrating the infarction area that is suppressed by stimulation of the vagus nerve in an embodiment of the present invention.

It became clear from analysis after four days that during stimulation of the vagus nerve, the infarct area was significantly reduced. That result was partially reversed by pacing (FIG. 3). The results of measuring the hemodynamics four days later are illustrated in Table 1.

TABLE 1

| Change in Hemodynamics 4 Days After Ischaemia Reperfusion | | | | |
|---|---|---|---|---|
| Electrocardiogram Data (Under Anesthesia) | | | | |
| Heart rate (bbp) | 417 ± 17 | 415 ± 7 | 417 ± 12 | 424 ± 11 |
| Left ventricular end-diastolic dimension (mm) | 5.4 ± 0.3 | 7.5 ± 0.5* | 6.6 ± 0.5*† | 6.6 ± 0.7* |
| Left ventricular end-systolic dimension (mm) | 2.6 ± 0.2 | 5.9 ± 0.6* | 4.4 ± 0.6*† | 5.1 ± 0.6* |
| Ejection fraction (%) | 51.5 ± 3.2 | 21.6 ± 4.2* | 31.7 ± 6.2*† | 23.9 ± 2.6* |
| Infarct wall thickness (mm) | 1.9 ± 0.2 | 1.3 ± 0.2* | 1.4 ± 0.2* | 1.3 ± 0.2* |
| Non-infarct wall thickness (mm) | 2.3 ± 0.3 | 1.9 ± 0.2* | 2.0 ± 0.2 | 1.9 ± 0.1* |
| Catheter Measurement Value (Under Anesthesia) | | | | |
| Heart rate (bpm) | 419 ± 8 | 409 ± 7 | 410 ± 14 | 424 ± 11 |
| Blood pressure (mmHg) | 119 ± 4 | 100 ± 5* | 102 ± 8* | 106 ± 7* |
| Left ventricular diastolic end pressure (mmHg) | 4.1 ± 1.6 | 7.2 ± 4.0* | 3.8 ± 2.1 | 4.6 ± 1.0 |
| Maximum left ventricular dp/dt (mmHg/s) | 13700 ± 1700 | 8300 ± 300* | 9900 ± 1800*† | 8300 ± 1000* |
| Minimum left ventricular dp/dt (mmHg/s) | −9700 ± 1600 | −6400 ± 700* | −7500 ± 1300* | −6400 ± 400* |

Figure 4:
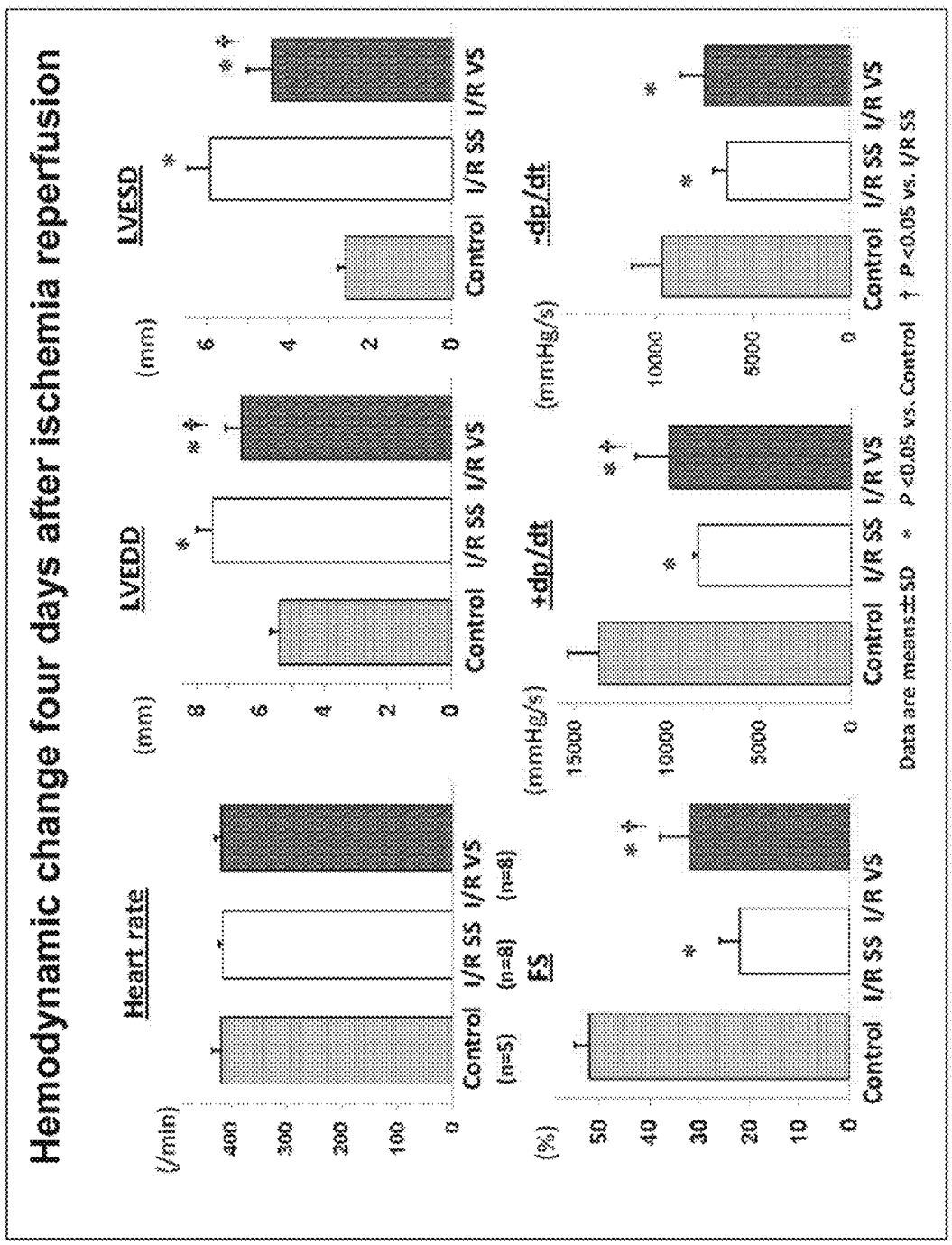
FIG. 4 is a table illustrating the hemodynamic change four days after ischemia reperfusion.

Data Notation: Average ± standard deviation
*P < 0.05 vs. Control SS (sham stimulation); †P < 0.05 vs. I/R SS A graph of the results in Table 1 is illustrated in FIG. 4. A change in heart rate was seen, however, it is thought that stimulation of the vagus nerve significantly suppressed an increase in the left ventricle and a drop in the ejection rate that occur after ischaemia reperfusion, and suppressed myocardial remodeling.

Figure 5:
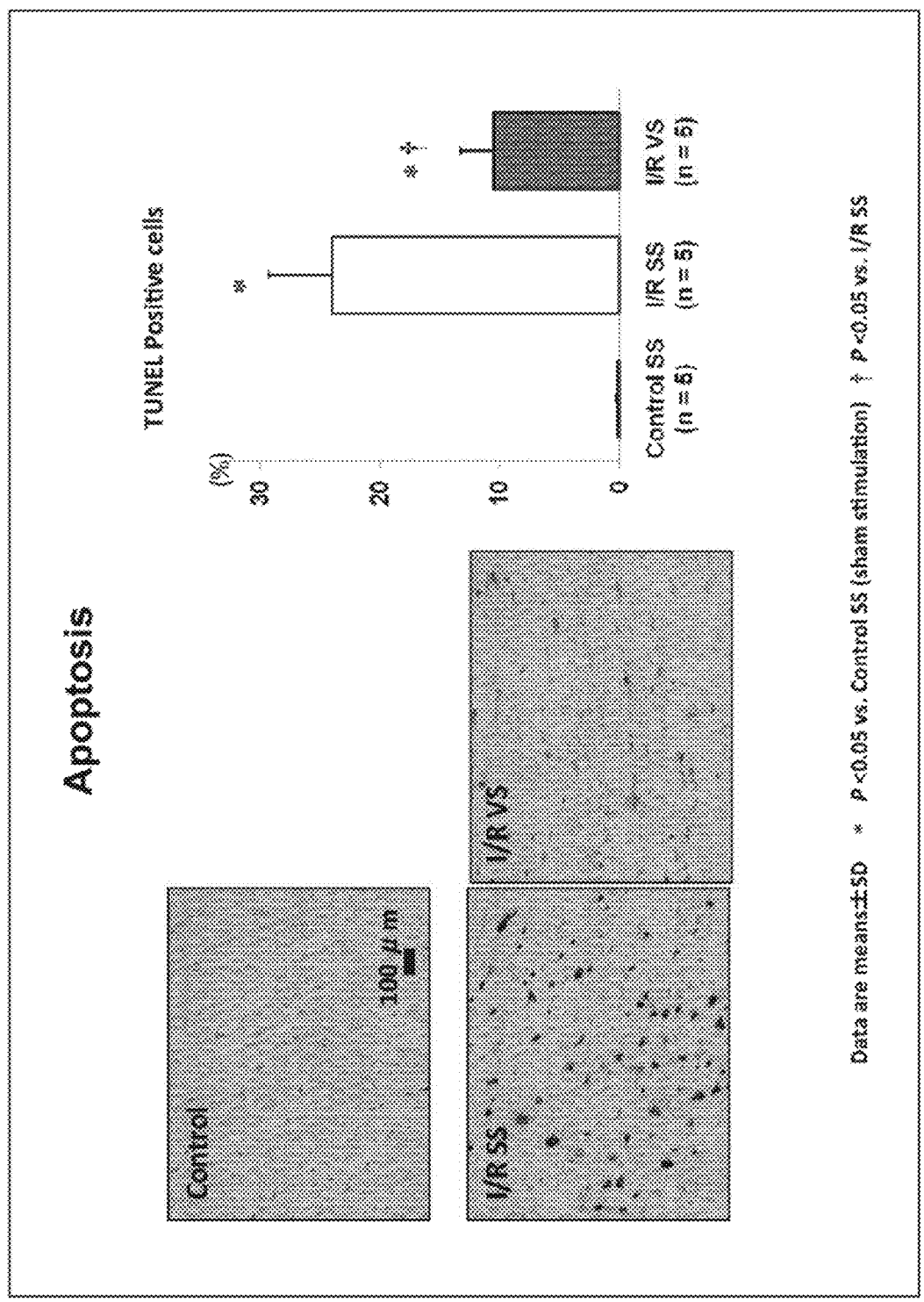
FIG. 5 is a drawing illustrating the ratio of TUNEL staining in the infarction area 24 hours after ischemia.
Figure 6:
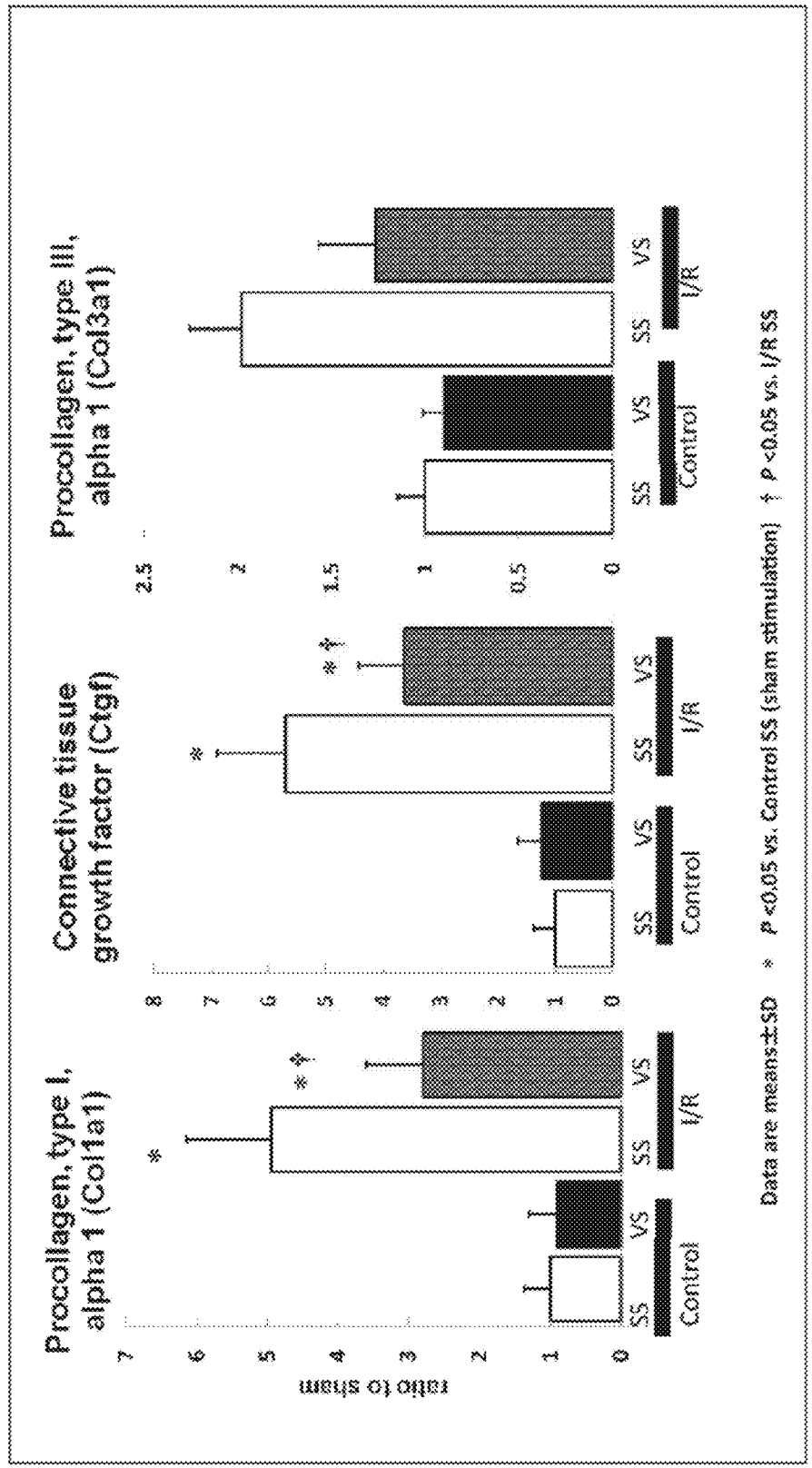
FIG. 6 is a drawing illustrating the expression of mRNA related to the production of collagen in the infarction site (measured using the real time PCR method).

Furthermore, the appearance of apoptosis at the myocardial infarction site was studied as the mechanism of the anti-modeling effect due to vagus nerve stimulation (FIG. 5). Multiple TUNEL positive cells appear in the infarct area 24 hours after due to ischaemia reperfusion, however, it was found that these TUNEL positive cell were significantly suppressed in the myocardial infarction area after vagus nerve stimulation Moreover, when mRNA was collected from the myocardial infarction 3 hours after the myocardial infarction, and the amount of gene expression related to the generation of collagen was measured, it was evident that gene expression recognized as procollagen, type 1, type 3, and the connective tissue growth factor were significantly suppressed by vagus nerve stimulation. The results are illustrated in FIG. 6.

As mentioned earlier, in treating cardiovascular disease using the present electrical stimulation device, the electrode is used to apply electrical stimulation by coming in direct contact with the vagus nerve of a human or an animal. Referring back to FIG. 7, the electrical stimulation site in the neck region is illustrated. When electrical stimulation is applied to a site of the vagus nerve by the electrode, the site of the vagus nerve to which the electrical stimulation is applied can be peeled back and exposed, for example, and the electrical stimulation can be applied by bringing the electrode in direct contact with the site. Examples of conventional electrode structures include a cylindrical shape. In this case, the cylindrical electrode is inserted into the site and placed longitudinally along the vagus nerve. However, the vagus nerve tends to be damaged upon contacting the edges around the top and bottom surfaces of the cylinder. In another conventional example, the electrode may be in the form of a wire. In this case, the wire electrode is wrapped around the vagus nerve for maximizing the stimulation effect and for stability. Again, the vagus nerve tends to be damaged during the wrapping operation of the thin wire.

Figure 10:
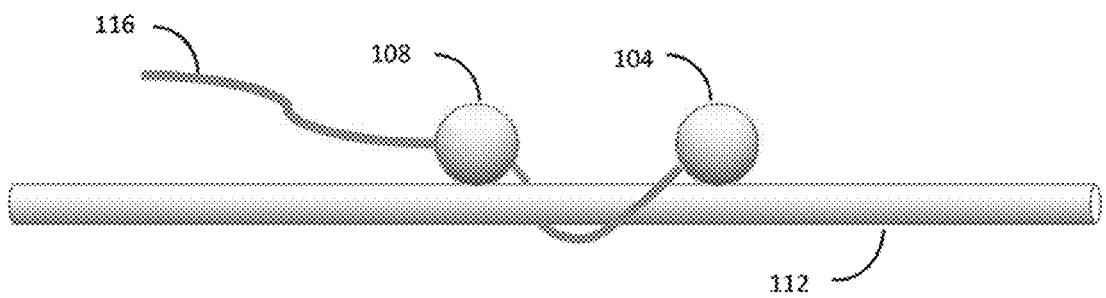
FIG. 10 illustrates an example of a configuration of two spherical electrodes in contact with the vagus nerve.

In view of the problems associated with the conventional electrode structures as above, a spherical electrode is devised for the purpose of reducing damages to the vagus nerve. FIG. 10 illustrates an example of a configuration of two spherical electrodes in contact with the vagus nerve. This example shows the case of applying a bipolar electrode having two spherical electrodes 104 and 108 for positive and negative nodes, both of which are placed in contact with the vagus nerve 112. These spherical electrodes are coupled to the electrical stimulation application unit via a connection wire 116. The number of spherical electrodes can be one or more depending on the desired level of electrical stimulation. As evident from FIG. 10, the damage to the vagus nerve 112 is likely to be minimal due to the electrodes that are spherical in shape.

It is to be understood that the above-described embodiments are illustrative of only a few of the many possible specific embodiments that can represent applications of the principles of the invention. Numerous and varied other arrangements can be readily devised by those skilled in the art without departing from the spirit and scope of the invention.

What is claimed is:

1. An electrical stimulation device for treating cardiovascular disease in a human or an animal, comprising:
   at least one electrode configured for placement on a nerve site inside the human or the animal, the at least one electrode having a spherical shape; and
   an electrical stimulation application unit coupled to the at least one electrode and configured to apply electrical stimulation to a vagus nerve in a neck region of the human or the animal by the at least one electrode.

2. The electrical stimulation device of to claim 1, wherein the cardiovascular disease is acute myocardial infarction; and
   the electrical stimulation device is used in conjunction with reperfusion therapy.

3. The electrical stimulation device of to claim 2, wherein the electrical stimulation device is configured to be controlled to start the electrical stimulation to the vagus nerve before the reperfusion therapy.

4. The electrical stimulation device of claim 1, wherein the electrical stimulation application unit is configured to apply electrical stimulation under conditions of a voltage of 0.1 to 5 V, a frequency of 1 to 30 Hz, and a pulse width of 500 μsec or greater.

5. The electrical stimulation device of claim 4, wherein an amount of time that the electrical stimulation application unit applies electrical stimulation is at least 0.5 hour and no greater than 10 hours.

6. A method for treating cardiovascular disease in a human or an animal comprising:
   placing at least one electrode in contact with a vagus nerve in a neck region of the human or the animal, the at least one electrode having a spherical shape; and
   applying electrical stimulation to the vagus nerve by the at least one electrode.

7. The method for of claim 6, wherein the cardiovascular disease is acute myocardial infarction.

8. The method claim 6, wherein the applying the electrical stimulation is used in conjunction with reperfusion therapy.

9. The method of claim 8, wherein the applying the electrical stimulation starts before the reperfusion therapy.

10. The method of claim 6, wherein the applying the electrical stimulation is performed under conditions of a voltage of 0.1 to 5 V, a frequency of 1 to 30 Hz, and a pulse width of 500 μsec or greater.

11. The method of claim 10, wherein an amount of time that the electrical stimulation application unit applies electrical stimulation is at least 0.5 hour and no greater than 10 hours.

* * * * *